United States Patent [19]

Kamath et al.

[11] 4,170,577

[45] Oct. 9, 1979

[54] 2,3-DIMETHYL-5-(2,2,3-TRIMETHYL-3-CYCLOPENTEN-1-YL)-2-PENTANOL PERFUME COMPOSITIONS

[75] Inventors: Venkatesh Kamath, Red Bank; Braja D. Mookherjee; Frederick L. Schmitt, both of Holmdel, all of N.J.

[73] Assignee: International Flavors & Fragrances Inc., New York, N.Y.

[21] Appl. No.: 968,040

[22] Filed: Dec. 8, 1978

Related U.S. Application Data

[62] Division of Ser. No. 893,542, Apr. 5, 1978.

[51] Int. Cl.² .............................................. C11B 9/00
[52] U.S. Cl. .................................... 252/522; 252/174; 252/174.11; 424/64; 424/69; 424/358
[58] Field of Search .......................................... 252/522

[56] References Cited

U.S. PATENT DOCUMENTS

4,052,341  10/1977  Naipawer et al. ................. 252/522

OTHER PUBLICATIONS

Chem. Ab. 72:125008b.

*Primary Examiner*—Veronica O'Keefe
*Attorney, Agent, or Firm*—Arthur L. Liberman; Franklin D. Wolffe

[57] ABSTRACT

2,3-Dimethyl-5-(2,2,3-trimethyl-3-cyclopenten-1-yl)-2-pentanol possesses a strong body woody, oily, sandalwood note reminiscent of sandalwood oil and is especially valuable in fragrance compositions, perfumed articles and colognes.

2 Claims, 4 Drawing Figures

IR SPECTRUM FOR EXAMPLE IA

NMR SPECTRUM FOR EXAMPLE IB
SOLVENT: CDCl₃
SWEEP WIDTH: 1500 Hz.

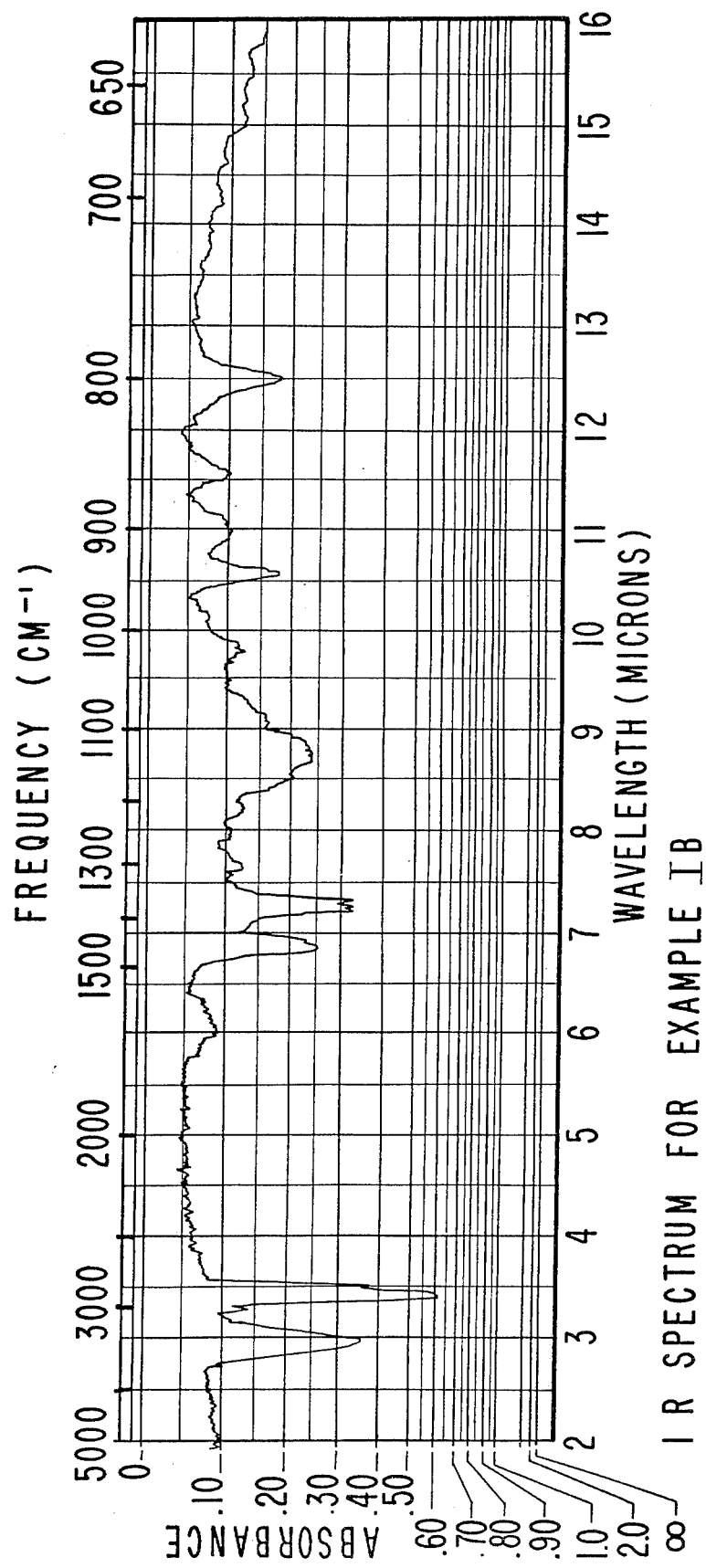

2,3-DIMETHYL-5-(2,2,3-TRIMETHYL-3-CYCLO-PENTEN-1-YL)-2-PENTANOL PERFUME COMPOSITIONS

This is a divisional of application Ser. No. 893,542, filed Apr. 5, 1978.

BACKGROUND OF THE INVENTION

According to Guenther (E. Guenther, "The Essential Oils", Vol. V, page 173, D. Van Nostrand Co. Inc., New York (1952), East Indian sandalwood oil "has been perhaps one of the most precious perfumery materials from antiquity down to modern times, and its popularity has shown no signs of waning." This oil is widely used in perfumery, and would be even more widely used except for its limited supply and high cost.

As is well known, a need exists for synthetic substances which can be used as sandalwood substitutes or extenders. It would be most desirable to be able to synthetically provide the major odorant compounds of the natural sandalwood oil, i.e. alpha-santalol and beta-santalol, but no commercially feasible route to these chemicals is known at this time.

It would be even more desirable to provide a synthetic compound which would have many of the desirable odor qualities of a fine East Indian sandalwood oil, yet not have the potentially labile primary allylic alcohol group present in the natural santalols. A compound which would be more resistant to acidic or oxidative decomposition as well as being base stable could be even more versatile than sandalwood oil itself.

There is no obvious explanation why only slight chemical changes should have such a dramatic effect on odor intensity other than to invoke the general unreliability of odor structure relationships. Why the addition or removal of a methyl group, the removal of a double bond or the mere moving of a methyl group would essentially destroy more than 90% of the odor intensity rather than merely cause subtle odor differences comparable to the subtle chemical differences cannot be explained by an theoretical concepts in the known art.

TABLE I

| Name | Structure |
|---|---|
| 3-Methyl-5-(2,2,3-trimethylcyclopent-3-en-1-yl)pentan-2-ol | 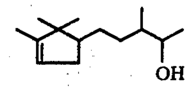 |
| 3-Methyl-5-(2,2,3-trimethylcyclopentan-1-yl)pentan-2-ol | 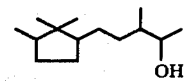 |
| 5-(2,2,3-Trimethyl-cyclopent-3-en-1-yl)pentan-2-ol | 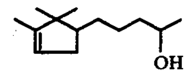 |
| 6-(2,2,3-Trimethyl-cyclopent-3-en-1-yl)hexan-3-ol | 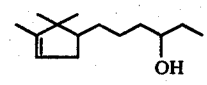 |
| 4-Methyl-6-(2,2,3-trimethylcyclopent-3-en-1-yl)hexan-3-ol | 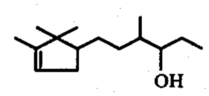 |
| 3-Ethyl-5-(2,2,3-trimethylcyclopent-3-en-1-yl)pentan-2-ol | 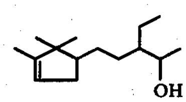 |
| 3-Methyl-5-(2,3,3-trimethylcyclopent-3-en-1-(R)-yl)pentan-2-ol | 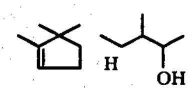 |
| 3-Methyl-5-(2,2,3-trimethylcyclopent-3-en-1-(S)-yl)pentan-2-ol | 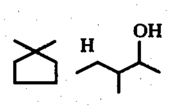 |
| 3-Methyl-5-(2,2,3-trimethylcyclopent-3-en-1-yl)pent-3-en-2-ol | 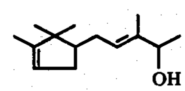 |

These materials are produced according to the reactions schemes:

TABLE II

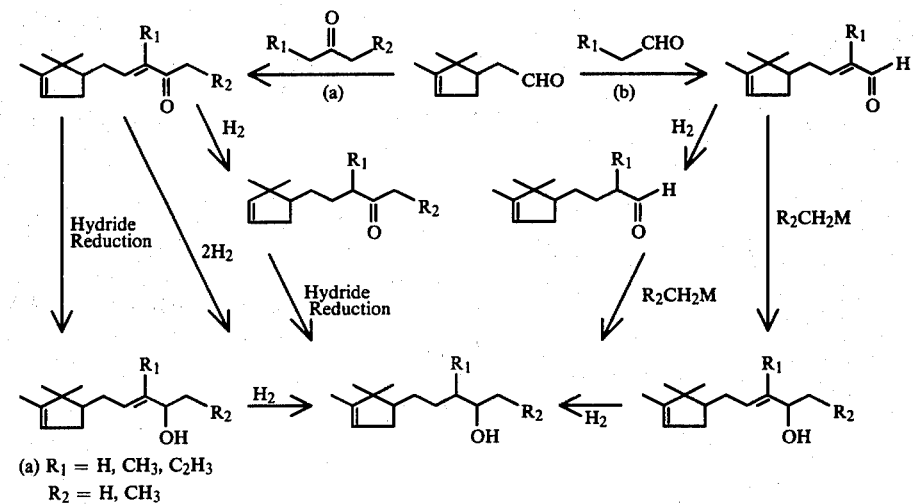

(a) $R_1$ = H, $CH_3$, $C_2H_3$
$R_2$ = H, $CH_3$

U.S. Pat. No. 4,052,341, issued on Oct. 4, 1977 provides a sandalwood type aroma imparting material having one of the structures:

East German Pat. No. 68,936 discloses for use in the sandalwood area a compound having the structure:

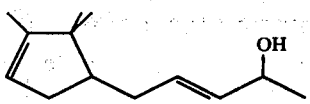

Furthermore, Chemical Abstracts Volume 72, 125008b sets forth a genus for the East German 68,936 encompasing the following group of compounds:

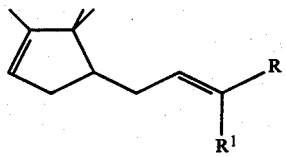

wherein R=CH$_2$OH, or —CHCH$_3$OH and R$^1$=H, CH$_3$ or C$_2$H$_5$

The 2,3-dimethyl-5-(2,2,3-trimethyl-3-cyclopenten-1-yl)-2-pentanol of our invention however, has unexpected, unobvious and advantageous properties in the sandalwood area not only insofar as the quality thereof is concerned but also insofar as the aroma strength and substantivity thereof is concerned. The "staying power" of 2,3-dimethyl-5-(2,3,3-trimethyl-3-cyclopenten-1-yl)-2-pentanol is unexpected, unobvious and advantageous.

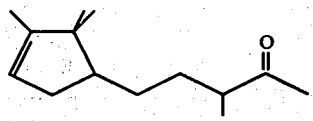

which is used in producing 2,3-dimethyl-5-(2,3,3-trimethyl-3-cyclopenten-1-yl)-2-pentanol and is, itself, produced according to Example 1A.

Figure 2:
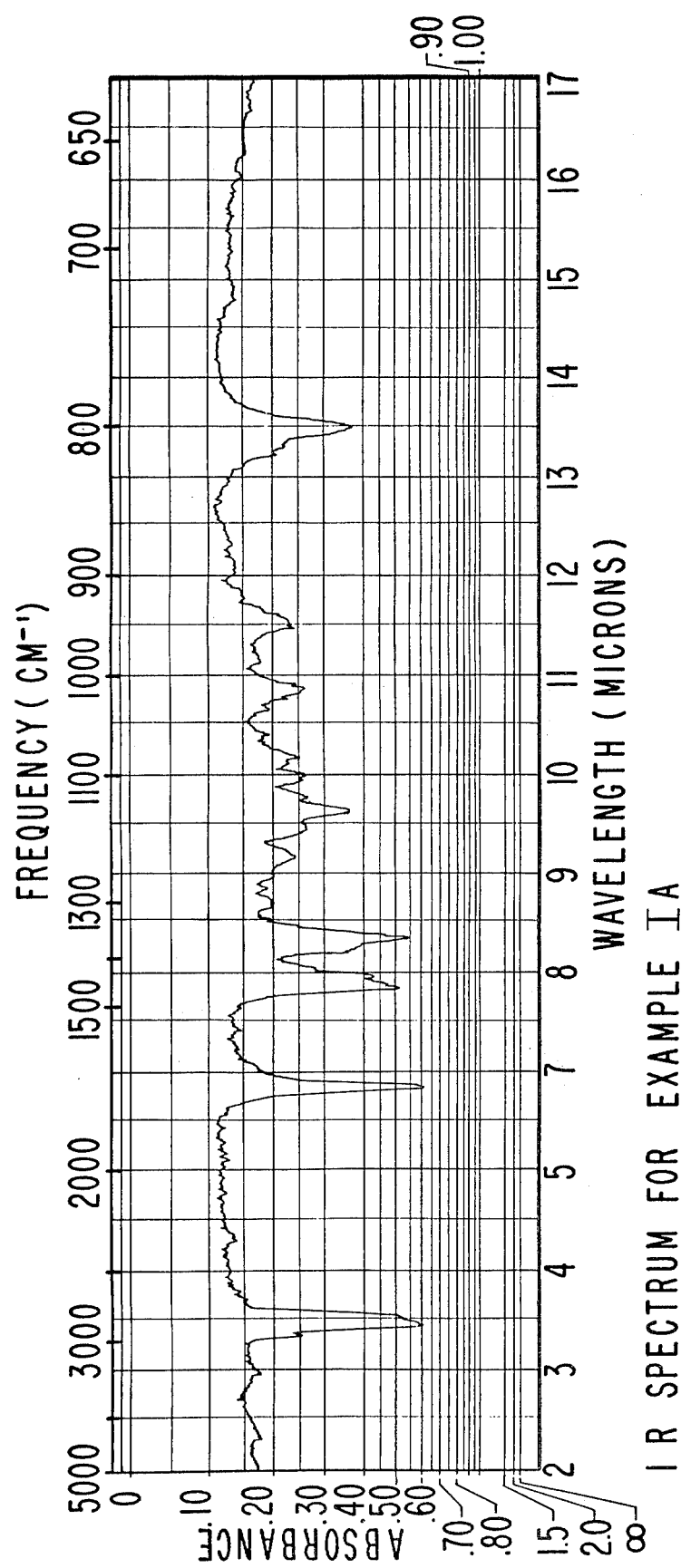

FIG. 2: The infrared spectrum for the intermediate ketone used in producing 2,3-dimethyl-5-(2,3,3-trimethyl-3-cyclopenten-1-yl)-2-pentanol, itself produced according to Example 1A.

Figure 3:
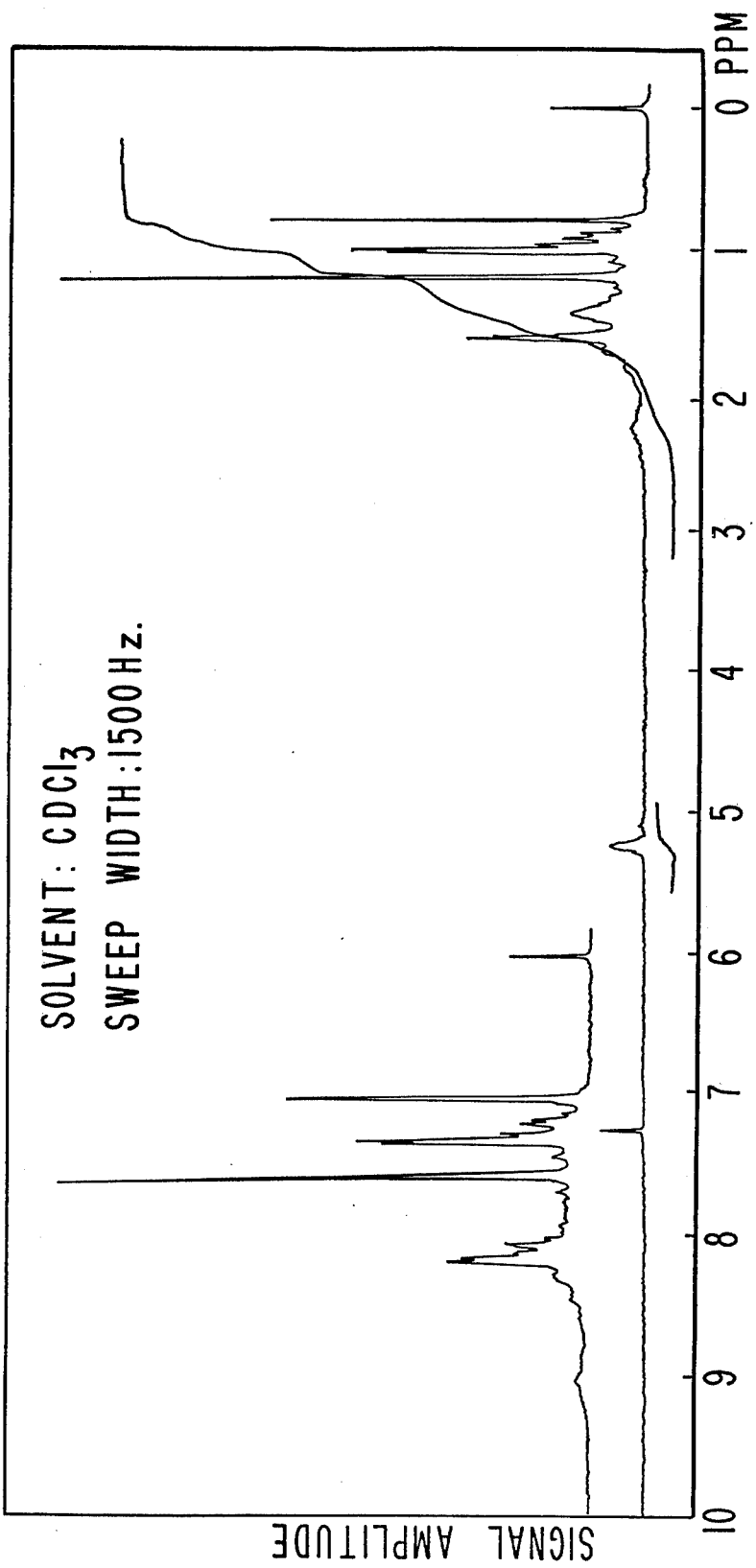

FIG. 3: The NMR spectrum for 2,3-dimethyl-5-(2,3,3-trimethyl-3-cyclopenten-1-yl)-2-pentanol produced according to Example 1B.

FIG. 4: The infrared spectrum for 2,3-dimethyl-5-(2,3,3-trimethyl-3-cyclopenten-1-yl)-2-pentanol produced according to the process of Example 1B.

THE INVENTION

In accordance with the present invention there are provided novel compositions comprising the novel compound 2,3-dimethyl-5-(2,3,3-trimethyl-3-cyclopenten-1-yl)-2-pentanol having the structure:

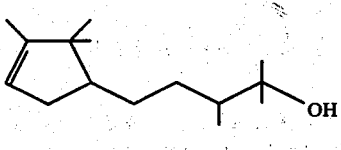

which is characterized by a long lasting woody, oily sandalwood aroma reminiscent of sandalwood oil and the naturally occuring santalols.

The invention also provides an economic and commercially feasible process from readily available and low cost starting materials for producing, 2,3-dimethyl-5-(2,3,3-trimethyl-3- cyclopenten-1-yl)-2-pentanol. The process for producing 2,3-dimethyl-5-(2,3,3-trimethyl-3-cyclopenten-1-yl)-2-pentanol is basically a three step reaction sequence as follows:

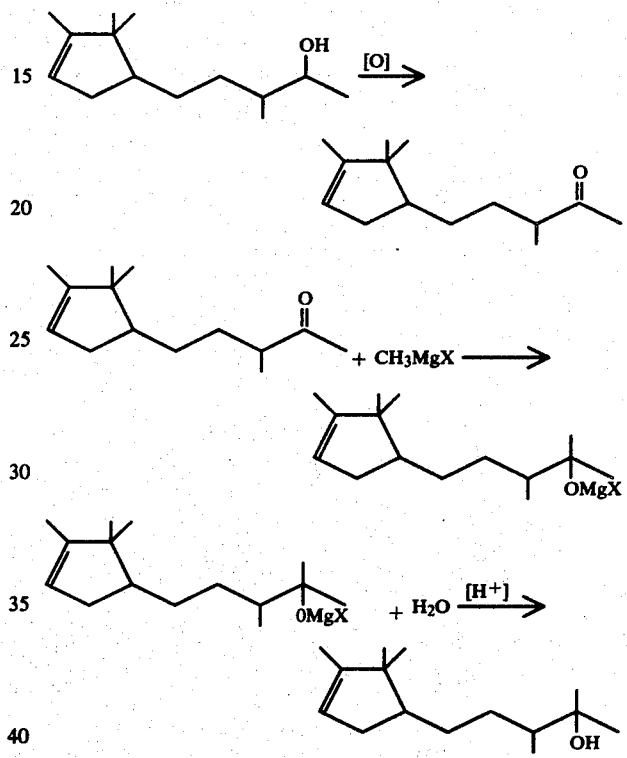

wherein X is iodo, chloro or bromo. The starting material, 3-methyl-5(2,2,3-trimethylcyclopent-3-en-1-yl)pentan-2-ol can be prepared according to the process of part 3 of Example VI at column 13, lines 50–68 of the U.S. Pat. No. 4,052,341 issued on Oct. 4, 1977. The oxidation of the starting material having the structure:

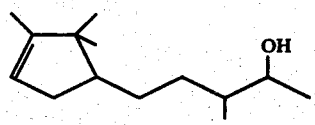

to form the intermediate ketone having the structure:

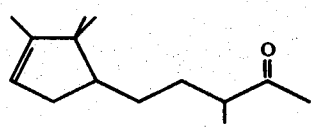

may be effected using any one of a number of oxidizing reagents, e.g. sodium dicromate, Jones reagent, potassium dicromate, air or oxygen itself. The most preferable oxidizing agent is sodium dicromate. Where the dicromate salt such as sodium dicromate is used it is most preferable to use it in admixture with concentrated sulfuric acid wherein the mole ratio of sodium dichromate:concentrated sulfuric acid is about 1:1. In addition the oxidizing agent such as sodium dichromate should be in a slight molar excess with respect to the material to be oxidized, the 3-methyl-5-(2,2,3-trimethyl-cyclopent-3-en-1-yl)pentan-2-ol. The reaction is carried out in an inert solvent such as toluene or xylene and in the presence of a small quantity of water. The resulting ketone may be purified from the reaction mass according to the standard techniques such as fractional distillation, or it may be used as is in a "crude" form and reacted with methyl magnesium halide, such as methyl magnesium bromide. The reaction of the ketone having the structure:

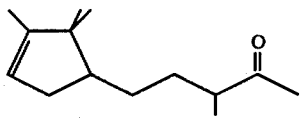

with a methyl magnesium halide, CH₃MgX wherein X is iodo, chloro or bromo will yield the organometalic intermediate having the structure:

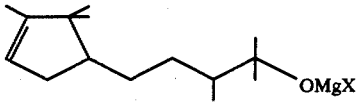

wherein X is iodo, chloro or bromo. This organometalic compound is a novel compound. The reaction of the methyl magnesium halide with the intermediate ketone having the structure:

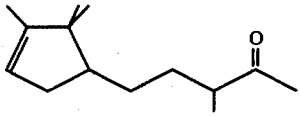

takes place in the presence of a volatile inert solvent such as tetrahydrofuran or diethyl ether. The reaction preferably takes place at a temperature of between −5° C. up to about 15° C.; preferably from 0° C. up to 10° C.

At the end of the reaction of the CH₃MgX with the intermediate ketone having the structure:

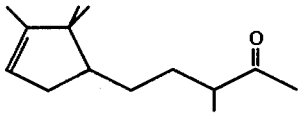

to form the organometalic compound having the structure:

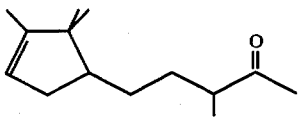

the said organometalic compound is then hydrolyzed in the presence of mineral acids such as hydrochloric acid, dilute sulfuric acid, dulute phosphoric acid, dilute nitric acid or dilute paratoluene sulfonic acid to form the desired 2,3-dimethyl-5-(2,2,3-trimethyl-3-cyclopenten-1-yl)-2-pentanol having the structure:

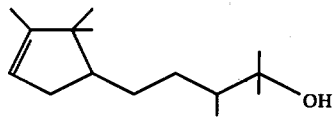

The hydrolysis reaction may take place at any convenient temperature between 0° C. and 40° C. with a preferred reaction temperature being room temperature, e.g. 20°-30° C. The reaction most conveniently takes place at atmospheric pressure but higher or lower pressures without adversely affecting the yield of product. At the end of the reaction the resulting product having the structure:

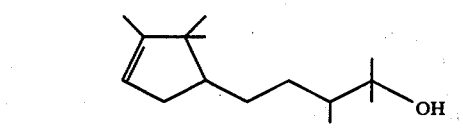

may be purified in a routine manner as by extraction and fractional distillation techniques.

The 2,3-dimethyl-5-(2,2,3-trimethyl-3-cyclopent-1-yl)-2-pentanol of our invention having a woody, oily and santalol like notes can be used to contribute sandalwood aromas.

As an olfactory agent the 2,3-dimethyl-5-(2,2,3-trimethyl-3-cyclopentn-1-yl)2-pentanol of this invention can be formulated into or used as components of a "perfume composition"

The term "perfume composition" is used herein to mean a mixture of organic compounds, including, for example, alcohols, aldehydes, ketones, nitriles, esters, and frequently hydrocarbons which are admixed so that the combined odors of the individual components produce a pleasant or desired fragrance. Such perfume compositions usually contain: (2) the main note of the "bouquet" or foundation-stone of the composition; (b) modifiers which round-off and accompany the main note: (c) fixatives which include odorous substances which lend a particular note to the perfume throughout all stages of evaporation, and substances which retard evaporation; and (d) top-notes which are usually low-boiling fresh smelling materials.

In perfume compositions the individual component will contribute its particular olfactory characteristics, but the overall effect of the perfume composition will be the sum of the effect of each ingredient. Thus, 2,3-dimethyl-5-(2,2,3-trimethyl-3-cyclopenten-1-yl)-2-pentanol of this invention, can be used to alter the aroma characteristics of a perfume composition, for example, by highlighting or moderating the olfactory reaction contributed by another ingredient in the composition.

The amount of 2,3-dimethyl-5-(2,2,3-trimethyl-3-cyclopenten-1-yl)-2-pentanol of this invention which will be effective in perfume compositions depends on many factors, including the other ingredients, their amounts and the effects which are desired. It has been found that perfume compositions containing as little as 2 percent of the 2,3-dimethyl-5-(2,3,3-trimethyl-3-cyclopenten-1-yl)-2-pentanol of this invention, or even less, can be used to impart a patchouli scent to soaps, cosmetics, and the other products. The amount employed can range up to 50 percent and higher and will depend on considerations of cost, nature of the end product, the effect desired on the finised product and particular fragrance sought.

The 2,3-dimethyl-5-(2,2,3-trimethyl-3-cyclopenten-1-yl)-2-pentanol of this invention can be used alone or in a perfume composition as an olfactory component in detergents and soaps, space odorants and deodorants; perfumes; colognes; toilet waters; bath salts; hair preparations such as lacquers, brilliantines, pomades, and shampoos; cosmetic preparations such as creams, deodorants, hand lotions, and sun screens; powders such as talcs, dusting powders, face powder and the like. When used as an olfactory component of a perfumed article, as little as 0.01 percent of the 2,3-dimethyl-5-(2,2,3-trimethyl-3-cyclopenten-1-yl)-2-pentanol will suffice to impart a key part of sandalwood aroma. Generally, no more than 0.5 percent is required.

In addition, the perfume composition can contain a vehicle or carrier for the 2,3-dimethyl-5-(2,2,3-trimethyl- 3-cyclopenten-1-yl)-2-pentanol alone or with other ingredients. The vehicle can be a liquid such as an alcohol such as ethanol, a glycol such as propylene glycol, or the like. The carrier can be an absorbent solid such as a gum or components for encapsulating the composition.

The following examples are given to illustrate embodiments of the invention as it is presently preferred to practice it. It will be understood that these examples are illustrative, and the invention is not to be considered as restricted thereto except as indicated in the appended claims. It is to be understood that unless otherwise stated all parts, proportions and percentages are by weight.

EXAMPLE I

PREPARATION OF 2,3-DIMETHYL-5-(2,2,3-TRIMETHYL-3-CYCLO-PENTEN-1-YL)-2-PENTANOL

Reaction sequence:

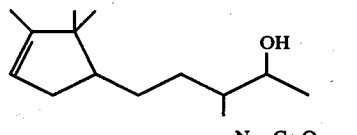

Na$_2$Cr$_2$O$_7$ →

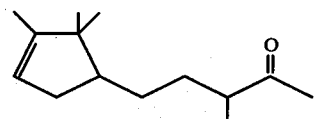

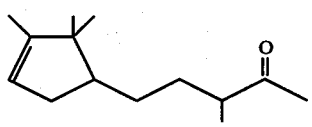

+ CH$_3$MgBr ──→

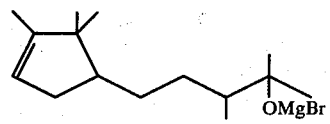

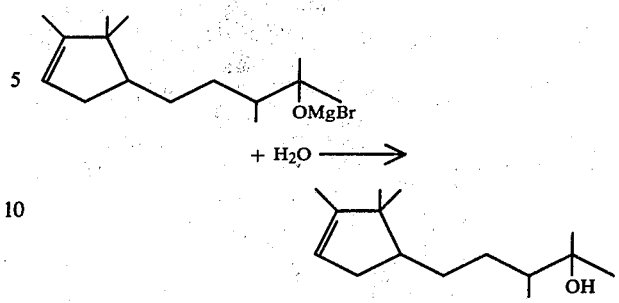

EXAMPLE IA 2.1 grams of 3-methyl-5-(2,3,3-trimethylcyclopent-3-en-1-yl)pentan-2ol(0.01 moles) and 25 ml toluene are admixed in a 50 ml round bottom flask equipped with thermometer, addition funnel and a magnetic stirrer. The resulting mixture is cooled to 5° C. and a solution of 3.3 grams sodium dicromate (0.011 moles) in 5 ml water and 1 ml concentrated sulfuric acid is slowly added thereto. The resulting reaction mass is stirred for a period of 0.5 hours at 5° C. using an ice bath to cool the reaction mass. The ice bath is then removed and the reaction mass is stirred at room temperature for an additional half hour. The reaction mass is then poured into a beaker containing 25 grams of ice. The resulting slurry is stirred and transferred to a 125 ml separatory funnel. The organic phase is separated from the aqueous phase and the organic phase is washed with 20 ml of a 5% sodium carbonate solution followed by three 25 ml portions of saturated sodium chloride solution. The resulting material is dried over anhydrous magnesium sulfate and filtered. The solvent is evaporated therefrom thereby obtaining 1.8 grams of crude intermediate ketone having the structure:

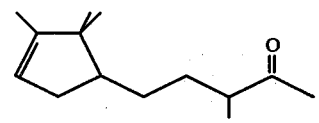

When the reaction is scaled up five fold (using 10.5 grams of 3-methyl-5-(2,2,3-trimethylcyclopent-3-an-1-yl)pentan-2-ol) 9.5 grams of the crude intermediate ketone having the structure:

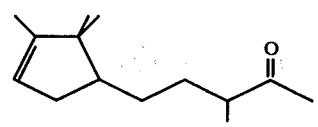

is obtained.

8.5 Grams of the ketone resulting from the five fold scale up is passed through 165 grams of 5% deactivated silicic acid and eluded with 5% ether/isopentane yielding 2 fractions, designated as "Fraction 1" and as "Fraction 2".

NMR and IR Analyses yield the information that the resulting material has the structure:

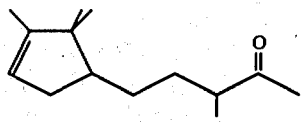

Figure 1:
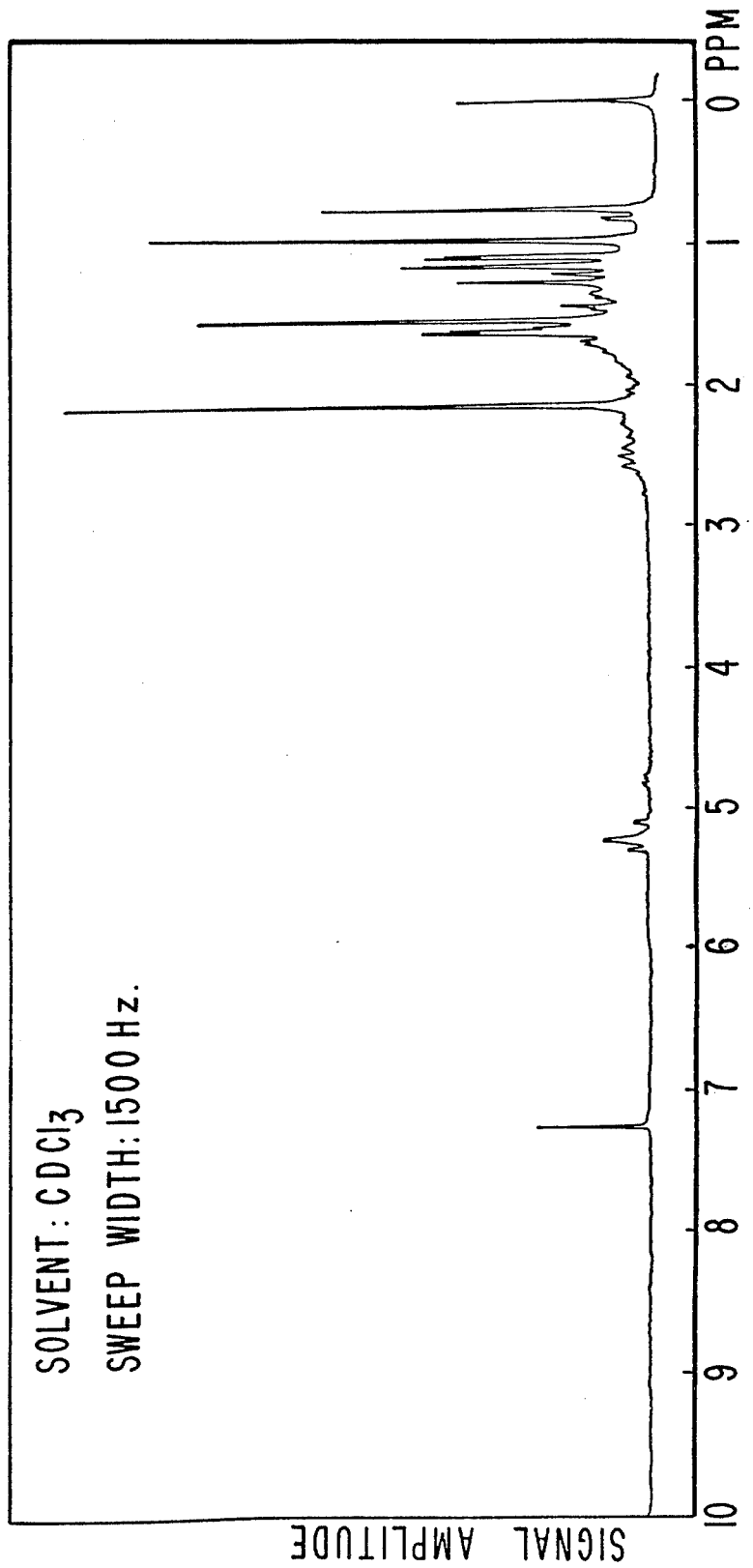
FIG. 1: The NMR Spectrum for the intermediate ketone, having the structure.

The NMR spectrum is set forth in FIG. 1. The IR spectrum is set forth in FIG. 2.

EXAMPLE IB 2.5 ml of methyl magnesium bromide (3 molar solution in diethylether) is placed in a 25 ml reaction flask fitted with a stirrer, thermometer, condenser and cooling bath. The methyl magnesium bromide solution is cooled to 5° C. and 1.5 grams of the ketone having the structure:

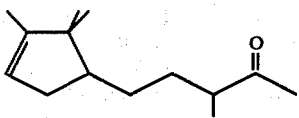

produced according to Example IA is added to the methyl magnesium bromide solution. The resulting reaction mass is stirred for a period of 30 minutes at 5° C. The cooling bath is then removed and the reaction mass is stirred for one hour at room temperature. The reaction mass is then poured into a beaker containing 20 grams of ice. The resulting organic layer is separated from the aqueous layer, and the organic layer is washed with a 5 molar aqueous solution of hydrochloric acid followed by washes of sodium chloride solution. The resulting material is dried and the solvent is removed yielding 1.5 grams of crude alcohol having the structure:

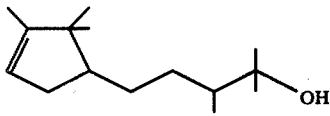

The crude material is injected onto a 10% carbowax column (10 ft. × ⅛) and the major peak is collected. The major peak has a good sandalwood note which is described as woody, oily and "santalol" isomer like.

The structure is confirmed using NMR and IR analyses. The NMR spectrum is set forth in FIG. 3. The infrared spectrum is set forth in FIG. 4.

EXAMPLE II

The following synthetic sandalwood oil formulation is produced:

| Ingredient | Parts by Weight |
|---|---|
| Amyrus Oil | 100 |
| Amyrus Acetate | 220 |
| Cedarwood Oil | 150 |
| Trans decahydro beta-naphthol Formate | 100 |
| Guaiophene (1% in diethyl phthalate) | 50 |
| Eugenol (10% in diethylphthalate) | 50 |
| Galaxolide ® (2.5% in diethyl phthalate) | 30 |
| Geranyl Phenyl Acetate | 50 |
| 2,3-dimethyl-5-(2,2,3-trimethyl-3-cyclopenten-1-yl)-2-pentanol | 250 |

The addition of 25% of 2,3-dimethyl-5-(2,2,3-trimethyl-3-cyclopenten-1-yl)-2-pentanol to the sandalwood formulation contributes the main sandalwood note to the fragrance. The odor of the fragrance without 2,3-dimethyl-5-(2,2,3-trimethyl-3-cyclopenten-1-yl)-2-pentanol is far distant from the desired odor of sandalwood.

EXAMPLE III

SANDAL PERFUME FORMULATION

The following mixture is prepared:

| Ingredients | Parts by Weight |
|---|---|
| 1',2',3',4',5',6',7',8',-octahydro-2',3',8',8'-tetramethyl-2'-acetonaphthone isomer mixture produced according to the process of Example VII of Application for U.S. Letters Pat. No. 434,948 filed on January 21, 1974 | 540 |
| Cedrenal - (A tricyclic sesquiterpinic aldehyde derived from cedrene, having the structure:<br>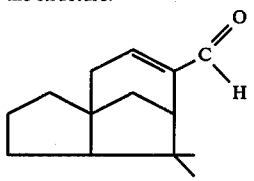<br>produced according to the process of U.S. Pat. Application 260,537 filed on June 7, 1972 (corresponding to published Dutch Appln. 7,307,849 laid open for public inspection on December 11, 1973) | 90 |
| Eugenol (1% in ethyl alcohol) | 54 |
| 2,5,5-trimethyl acetyl cycloheptane produced according to Example I of U.S. Pat. Application 349,180 filed on April 9, 1973 | 180 |
| Borneol (1% in ethyl alcohol) | 18 |
| Hexahydro-4,7-methanoindane-2-carboxaldehyde | 18 |
| 2,3-Dimethyl-5-(2,2,3-trimethyl-3-cyclopenten-1-yl)-2-pentanol<br>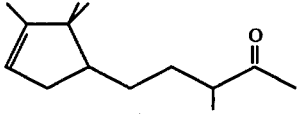<br>produced according to Example IB | 100 |

The 2,3-dimethyl-5-(2,2,3-trimethyl-3-cyclopenten-1-yl)2-pentanol imparts the woody, oily santalol like note of sandal to the formulation

EXAMPLE IV

PREPARATION OF A SOAP COMPOSITION

A total of 100 g of soap chips produced from unperfumed sodium base toilet soap made from tallow and coconut oil are mixed with 1 g of the perfume composition set forth in Example III until a substantially homogeneous composition is obtained. The soap composition manifests a characteristic "sandal cologne" aroma having

EXAMPLE V

PREPARATION OF A SOAP COMPOSITION

A total of 100 g of soap chips produced from unperfumed sodium base toilet soap made from tallow and coconut oil is mixed with 1 g of tricyclene-9-butenone produced according to Example III until a substantially homogeneous composition is obtained. The soap composition manifests a woody, oily sandalwood oil character.

EXAMPLE VI

PREPARATION OF A DETERGENT COMPOSITION

A total of 100 g of a detergent powder sold under the trademark "RINSO" are mixed with 0.15 g of a perfume composition containing the mixture obtained in Example III until a substantially homogeneous composition having a "sandal cologne" fragrance with woody, oily and santalol like notes is obtained.

EXAMPLE VII

PREPARATION OF A COSMETIC BASE

A cosmetic powder is prepared by mixing 100 g of talcum powder with 0.25 g of the perfume composition of Example III in a ball mill. A second cosmetic powder is similarly prepared except that the mixture produced in Example III is replaced with the product produced in Example IB. The cosmetic powder containing the material of Example III has a "sandal cologne" fragrance with a woody, oily, santalol like character. The cosmetic powder produced using this material of Example IB also has a sandalwood aroma with woody, oily and santalol like nuances.

EXAMPLE VIII

LIQUID DETERGENT CONTAINING TRICYCLENE-9-BUTENONE

Concentrated liquid detergents with a sandalwood-like odor containing 0.2%, 0.5% and 1.2% of the product produced in accordance with the process of Example IB are prepared by adding the appropriate quantity of 2,3-dimethyl-5-(2,2,3-trimethyl-3-cyclopenten-1-yl)-2-pentanol to the liquid detergent known as P-87. The sandalwood aroma of the liquid detergent increases with increasing concentration of the 2,3-dimethyl-5-(2,2,3-trimethyl-3-cyclopenten-1-yl)-2-pentanol of this invention.

EXAMPLE IX

PREPARATION OF COLOGNE AND HANDERCHIEF PERFUME

The composition of Example III is incorporated in a cologne having a concentration of 2.5% in 85% aqueous ethanol; and into a handkerchief perfume in a concentration of 20% (in 95% ethanol). The use of the composition of Example III affords a distinct and definite "sandal cologne" aroma having a warm sandalwood-like character to the handkerchief perfume and to the cologne.

EXAMPLE X

COLOGNE AND HANDKERCHIEF PERFUME

The 2,3-dimethyl-5-(2,2,3-trimethyl-3-cyclopenten-1-yl)-2-pentanol produced by the process of Example IB is incorporated into a cologne having a concentration of 2.5% in 85% ethanol; and into a handkerchief perfume in a concentration of 10% (in 95% ethanol). The 2,3-dimethyl-5-(2,2,3-trimethyl-3-cyclopenten-1-yl)-2-pentanol produced in Example IB affords a distinct and definite sandalwood aroma with woody, oily and santalol-like notes to the handkerchief perfume to the cologne.

What is claimed is:

1. A perfume composition comprising a perfuming agent of a compound having the structure:

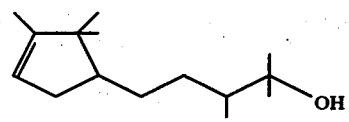

and an adjuvant therefor selected from the group consisting of aldehydes, alcohols other than the compound having the structure:

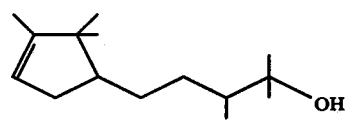

ketones, lactones, nitriles, carboxylic acid esters, ethers and natural essential oils.

2. A cologne comprising the compound having the structure:

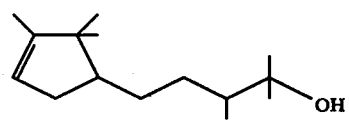

ethanol and water.